US 6,709,432 B2

(12) United States Patent
Ferek-Patric

(10) Patent No.: US 6,709,432 B2
(45) Date of Patent: Mar. 23, 2004

(54) ABLATION METHODS AND MEDICAL APPARATUS USING SAME

(75) Inventor: Bozidar Ferek-Patric, Zagreb (HR)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 10/132,509

(22) Filed: Apr. 26, 2002

(65) Prior Publication Data

US 2003/0204184 A1 Oct. 30, 2003

(51) Int. Cl.[7] ............................................ A61B 18/18
(52) U.S. Cl. ............................................ 606/41; 128/898
(58) Field of Search .................................... 606/32–52

(56) References Cited

U.S. PATENT DOCUMENTS

| | | | |
|---|---|---|---|
| 4,763,646 A | 8/1988 | Lekholm | |
| 5,196,006 A | * 3/1993 | Klopotek et al. | 606/32 |
| 5,261,418 A | 11/1993 | Ferek-Petric | |
| 5,271,392 A | 12/1993 | Ferek-Petric | |
| 5,606,974 A | * 3/1997 | Castellano et al. | 600/462 |
| 5,733,281 A | 3/1998 | Nardella | |
| 5,840,030 A | 11/1998 | Ferek-Petric et al. | |
| 6,032,067 A | * 2/2000 | Sjoholm | 600/407 |
| 6,206,874 B1 | * 3/2001 | Ubby et al. | 606/34 |
| 6,286,512 B1 | * 9/2001 | Loeb et al. | 128/898 |
| 6,468,271 B1 | * 10/2002 | Wentzel et al. | 606/34 |

FOREIGN PATENT DOCUMENTS

WO  WO 99/04709  * 2/1999  .......... A61B/17/36

* cited by examiner

Primary Examiner—Roy D. Gibson
Assistant Examiner—Peter Vrettakos
(74) Attorney, Agent, or Firm—Girma Wolde-Michael; Michael C. Soldner

(57) ABSTRACT

Apparatus and methods of the present invention utilize sensed acoustical energy and may detect both instability of an ablation electrode during the ablation process and/or crater formation during tissue ablation.

38 Claims, 10 Drawing Sheets

ABLATION METHODS AND MEDICAL APPARATUS USING SAME

FIELD OF THE INVENTION

The present invention relates to ablation methods and apparatus, e.g., such as those used for cardiac therapy. More particularly, the present invention pertains to apparatus and methods that use monitoring of acoustic energy to control and/or provide information regarding ablation processes.

BACKGROUND

Catheters for electromagnetic ablation are known and are commonly used to treat various diseases and medical disorders. Typically, the catheter includes an energy-delivering electrode that is coupled to a source of electromagnetic energy, e.g., an electrosurgical generator. Other electrodes can be proximally positioned on the catheter and can be used for sensing and other related electrical purposes. The generator energizes the electrode, which then transfers the energy to tissue disposed adjacent thereto. The surgical energy is typically applied to the tissue at a selected level and for a selected duration to effect a biological change in the tissue.

In prior procedures, the ablation catheter is employed to alter tissue. In order to ablate the tissue, electromagnetic energy is applied to create a lesion via the energy-delivering electrode without regard to the specific level of electromagnetic energy supplied by the generator. In situations where too much electromagnetic energy is delivered to the tissue during the electrosurgical procedure, the tissue "pops," thus indicating the application of an excessive amount of energy.

As such, when the ablation electrode has firm contact with tissue and high power is applied, an undesirable crater may be formed at the contact site. When crater formation occurs, electromagnetic energy directed by the ablation electrode causes cells within the tissue to explode, thus creating the popping sound that may even be heard outside the patient's body. Crater formation may cause an uncontrolled high-volume lesion. To further patient safety, prevention of crater formation is desired because it is unknown how much of an effect crater formation has on the occurrence of thromboembolic incidents.

In other words, high-strength electromagnetic energy can cause tissue cells to be undesirably destroyed during certain medical procedures, e.g., ablation. As such, the delivery of such energy needs to be effectively controlled.

Further, electrosurgery cutters and ablation catheters use such electromagnetic energy. While a cut with an electrosurgical cutter is very deep and performed relatively fast, an ablation lesion formed by an ablation catheter should be precise. In other words, lesion size should also be controlled, and at least one way to control lesion size is to control the delivery of the energy to the ablation site.

Therefore, for at least the above reasons, some ablation systems known in the art include sophisticated power control systems. Such control systems use various techniques to monitor the ablation process and control the delivery of energy to the desired ablation site.

For example, catheters including temperature measurement sensors allow for control of an ablation energy generator such that an appropriate constant temperature of the ablation electrode can be maintained. However, when the temperature is low, the lesion may not be sufficient to effectively destroy the tissue. If the temperature rises too high, e.g., above 70 degrees Celsius, coagulation on the electrode may occur and undesirably increase the impedance of the ablation system.

Further, for example, U.S. Pat. No. 5,733,281 to Nardella entitled "Ultrasound and Impedance Feedback System for Use with Electrosurgical Instruments," issued Mar. 31, 1998, discloses an electrosurgical feedback system that includes an acoustical detection element and/or an impedance determination circuit. The acoustical detection element may include an ultrasonic transducer that acoustically detects the effects of energy on tissue, such as the generation of steam created during the heating process. The acoustical detection element generates an acoustic output signal that may regulate the application of power to an energy delivering electrode. Nardella further discloses that the acoustical detection element may include a microphone coupled to a speaker for producing an audible output signal.

Various other problems may also be present in an ablation process. For example, to use the maximal amount of ablation energy, the energy-delivering electrode preferably should have an intimate contact with the cardiac tissue. Because of cardiac contractions, dislodgement of the electrode from the desired position may occur.

Electrophysiologists usually monitor intracardiac potentials to confirm the proper position (e.g., stability of) as well as the proper contact of the electrode with tissue, e.g., the endocardium. However, the intracardiac potential is discontinuous, being characterized with intrinsic deflection that is repetitive at the frequency of heart beats. Distinct ST wave amplitude elevation caused by the injury current may be used to confirm the pressure of the electrode to the cardiac muscle. However, dislodgement may also occur anywhere within the cardiac cycle while there is no intracardiac signal.

Table 1 below lists U.S. Patents relating to various ablation techniques.

TABLE 1

| Patent No. | Inventor | Issue Date |
| --- | --- | --- |
| 5,840,030 | Ferek-Petric et al. | Nov. 24, 1998 |
| 5,733,281 | Nardella | Mar. 31, 1998 |
| 4,763,646 | Lekholm | Aug. 16, 1988 |

All documents listed in Table 1 above, and further elsewhere herein, are hereby incorporated by reference herein in their respective entireties. As those of ordinary skill in the art will appreciate readily upon reading the Summary of the Invention, Detailed Description of the Embodiments, and claims set forth below, many of the devices and methods disclosed in the documents of Table 1 and other documents incorporated by reference herein may be modified advantageously by using the teachings of the present invention.

SUMMARY OF THE INVENTION

The present invention has certain objects. That is, various embodiments of the present invention provide solutions to one or more problems existing in the art with respect to ablation of tissue. One such problem involves the inadvertent creation of an ablation crater. Another problem involves lack of stability of an ablation catheter during ablation due to physiological events, e.g., heart contractions.

In comparison to known ablation techniques, various embodiments of the present invention may provide certain advantages. For example, the present invention provides apparatus and methods that enable a practitioner to acoustically monitor ablation of tissue and control the amount of electromagnetic energy directed to the tissue to prevent crater formation. Further, the present invention provides systems and methods that increase stability of an ablation catheter during ablation by acoustically monitoring ablation and indicating instability to the practitioner. Further, the present invention provides systems and methods for monitoring both acoustical energy and temperature during ablation to aid in preventing crater formation.

Some embodiments of the present invention may provide one or more of the following features for ablating tissue: providing a catheter including an ablation electrode; ablating tissue using an ablation electrode, wherein the ablation electrode directs electromagnetic energy to the tissue; detecting at least acoustical energy resulting from ablation of tissue (e.g., cardiac tissue); comparing detected acoustical energy to at least a portion of an ECG waveform to determine stability of a catheter; determining whether detected acoustical energy is synchronized with at least a portion of an ECG waveform; controlling electromagnetic energy directed to tissue based on comparing detected acoustical energy to at least a portion of an ECG waveform; detecting at least acoustical energy resulting from ablation of tissue using a piezoelectric transducer element; detecting an ablation temperature using a piezoelectric transducer element; controlling electromagnetic energy directed to tissue based on a detected ablation temperature; simultaneously controlling electromagnetic energy directed to tissue based on detected acoustical energy and detected ablation temperature; analyzing detected acoustical energy to detect at least one popping sound; reducing electromagnetic energy directed to tissue if at least one popping sound is detected; removing at least a cardiac generated acoustical energy component from a transducer signal; controlling electromagnetic energy directed to tissue based on a transducer signal having at least a cardiac generated acoustical energy component removed therefrom; comparing a transducer signal to a predetermined popping sound spectrum to determine the presence of a popping sound; reducing electromagnetic energy directed to tissue if a transducer signal and at least a portion of an ECG waveform are asynchronous; and triggering an electrode stability alarm if a transducer signal and at least a portion of an ECG waveform are synchronous.

Some embodiments of the present invention may provide one or more of the following additional features for ablating tissue: providing a catheter including an ablation electrode and a tensiometric element; detecting a plurality of cardiac contractions using a tensiometric element and providing a tensiometric signal representative of a plurality of cardiac contractions; controlling electromagnetic energy directed to cardiac tissue based on a compared tensiometric signal and transducer signal; and detecting acoustical energy, wherein the detected acoustical energy includes a plurality of sound events, wherein comparing a tensiometric signal to a transducer signal includes measuring a time interval between at least one sound event and at least one cardiac contraction.

Further, some embodiments of the present invention include one or more of the following features for an ablation apparatus: a catheter body; an ablation electrode proximate a distal end of a catheter body, wherein the ablation electrode is operable to direct electromagnetic energy to tissue; a piezoelectric transducer element proximate a distal end of a catheter body, wherein the piezoelectric transducer element is operable to detect acoustical energy and temperature and provide a transducer signal representative of detected acoustical energy and temperature; an ablation electrode that includes a ring electrode including an outer radial surface and an inner radial surface, wherein the inner radial surface defines an inner volume, wherein a piezoelectric transducer element is located proximate the inner volume of the ablation electrode, and further wherein the piezoelectric transducer element is acoustically coupled to the inner radial surface of the ablation electrode; a piezoelectric transducer element that includes a piezoelectric film having an inner radial surface and an outer radial surface, wherein the outer radial surface of the piezoelectric film is acoustically coupled to the inner radial surface of an ablation electrode by a conductive adhesive layer; a detection sensor operable to detect acoustical energy; controller circuitry in communication with sensing circuitry and a detection sensor, wherein the controller circuitry is operable to compare detected acoustical energy to an electrocardiogram to determine stability of a catheter when the catheter is positioned for performing an ablation process; and controller circuitry operable to control electromagnetic energy directed by an ablation electrode to tissue based on detected acoustical energy and an electrocardiogram.

Some embodiments of the present invention include one or more of the following additional features for an ablation apparatus: a detection sensor including a piezoelectric transducer element; a catheter that includes a catheter body, wherein a piezoelectric transducer element is positioned proximate an ablation electrode of the catheter; controller circuitry operable to remove at least a cardiac generated acoustical energy component from a transducer signal and to detect at least one popping sound based on the transducer signal having the at least a cardiac generated acoustical energy component removed therefrom; controller circuitry operable to compare a transducer signal to an acoustic profile representative of a popping sound and reduce electromagnetic energy directed to tissue if the transducer signal includes at least one popping sound; controller circuitry operable to simultaneously control electromagnetic energy directed to tissue based on detected acoustical energy and detected ablation temperature; controller circuitry operable to detect at least one popping sound based on a comparison between a transducer signal having at least a cardiac generated acoustical energy component removed therefrom and an acoustic profile representative of a popping sound; controller circuitry operable to measure a sound intensity of detected acoustical energy based on a transducer signal; controller circuitry operable to compare a transducer signal to at least a portion of an ECG waveform signal if a measured sound intensity is greater than a sound intensity threshold; is controller circuitry operable to reduce electromagnetic energy directed to tissue if a transducer signal and at least a portion of an ECG waveform signal are asynchronous; and controller circuitry operable to trigger an electrode stability alarm if a transducer signal and at least a portion of an ECG waveform signal are synchronous.

Some embodiments of the present invention include one or more of the following additional features for an ablation apparatus: a catheter including an elongated catheter body, an ablation electrode proximate at a distal end thereof, and a tensiometric element lying along a length of the catheter body, wherein the ablation electrode is operable to direct electromagnetic energy to cardiac tissue, and further wherein the tensiometric element is operable to provide a tensiometric signal representative of a plurality of cardiac contractions; controller circuitry operable to compare a tensiometric signal to a transducer signal; controller circuitry operable to control electromagnetic energy directed to cardiac tissue based on a comparison between a tensiometric signal and a transducer element; and controller circuitry operable to measure a time interval between at least one cardiac contraction and at least one sound event of a plurality of sound events of detected acoustical energy.

The above summary of the invention is not intended to describe each embodiment or every implementation of the present invention. Rather, a more complete understanding of the invention will become apparent and appreciated by reference to the following detailed description and claims in view of the accompanying drawings.

BRIEF DESCRIPTION OF THE DRAWINGS

The present invention will be further described with reference to the drawings, wherein.

DETAILED DESCRIPTION OF THE EMBODIMENTS

Figure 1:
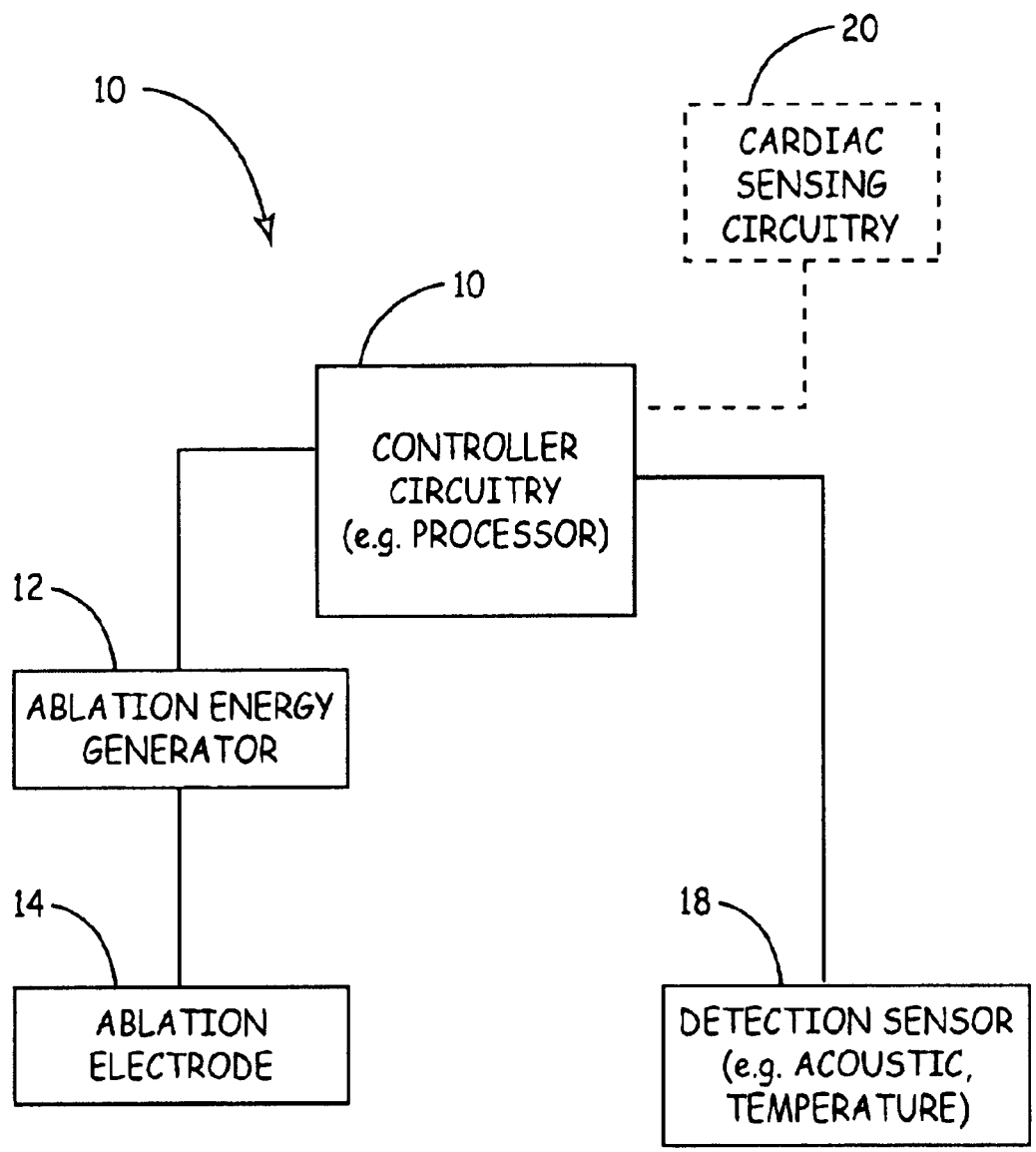
FIG. 1 is a block diagram depicting an illustrative ablation system according to one embodiment of the present invention.

FIG. 1 is a block diagram depicting an illustrative ablation system 10 according to one embodiment of the present invention. Ablation system 10 includes controller circuitry 10, ablation energy generator 12 in communication with the controller circuitry 10, and an ablation electrode 14 in communication with the ablation energy generator 12.

The ablation energy generator 12 provides energy and directs the energy to the ablation electrode 14 for ablating tissue. Any suitable generator known in the art may be used in accordance with the present invention, e.g., DC energy pulse from a standard defibrillator, RF transmitter, microwave transmitter, laser light source, etc. Further, any suitable type of energy used for ablating tissue may be used in accordance with the present invention, e.g., radiofrequency energy, laser energy, microwave energy, chemical energy, etc.

Ablation system 10 also includes detection sensor 18 in communication with controller circuitry 10. Detection sensor 18 is operable to detect one or more various physiological and/or non-physiological parameters for assisting in ablation of tissue, e.g., ablation temperature, acoustical energy produced by ablation, etc.

Various types of sensors known in the art may be used in accordance with the present invention and depend upon the parameter to be detected. For example, detection sensor 18 may include a microphone for detecting acoustical energy, an ultrasound element for sending ultrasound waves and receiving reflected ultrasound waves, a temperature sensor for measuring temperature of the ablation electrode during ablation, and a piezoelectric transducer element. Preferably, sensor 18 is a microphone, more preferably a contact microphone, and even more preferably a contact microphone capable of use in sensing temperature and sound.

The detection sensor 18 is operable to detect a desired parameter and provide a signal representative of the detected parameter to the controller circuitry. Various types of sensors, e.g., contact microphone, piezoelectric transducer elements, etc., that may be used in accordance with the present invention will be further described below.

The controller circuitry 10, which is in communication with the detection sensor 18 and the ablation energy generator 12, is operable to recognize various sensed signals, perform various analysis and/or detection functions, perform filtering functions, as well as provide any necessary conversion, processing, or other manipulations of signals, data, information, etc., as may be required to carry out the functionality of the present invention, as described herein in greater detail. Controller circuitry 10 may include any processor-based circuitry or any other logic and control circuitry known in the art capable of providing such functionality.

The controller circuitry 10 may be any suitable combination of processors, memory, analyzers, digital circuitry, and/or filters known in the art. For example, controller circuitry 10 may be processor-based and may be programmed to perform various types of analysis known in the art, e.g., Fourier analysis, wavelet transformation, averaging, integration, etc.

Ablation system 10 may optionally include cardiac sensing circuitry 20. The cardiac sensing circuitry 20, for example, may be operable to detect atrial and/or ventricular activity and provide an ECG waveform signal representative of such cardiac activity. Cardiac sensing circuitry 20 may include any suitable circuitry known in the art for detecting cardiac activity. For example, cardiac sensing circuitry 20 may include sense amplifiers, threshold setting circuitry, and/or comparator/threshold circuitry, as well as any other cardiac monitoring devices that may provide information used to monitor the ablation processes as described herein.

In order to facilitate tissue ablation, e.g., within the heart, the ablation electrode 14 may be attached to or form a part of a catheter or other medical device operable to be inserted for positioning in contact with heart tissue. The ablation electrode may be any suitable ablation electrode known in the art, e.g., plate or ring electrodes as is described in U.S. Pat. No. 5,840,030 to Ferek-Petric et al. entitled "Ultrasound Marked Cardiac Ablation Catheter," issued on Nov. 11, 1998, dome electrodes, microwave antenna, laser light lens, etc. Further, the ablation electrode 14 may be manufactured using any suitable material known in the art, e.g., platinum and various platinum alloys.

Figure 2:
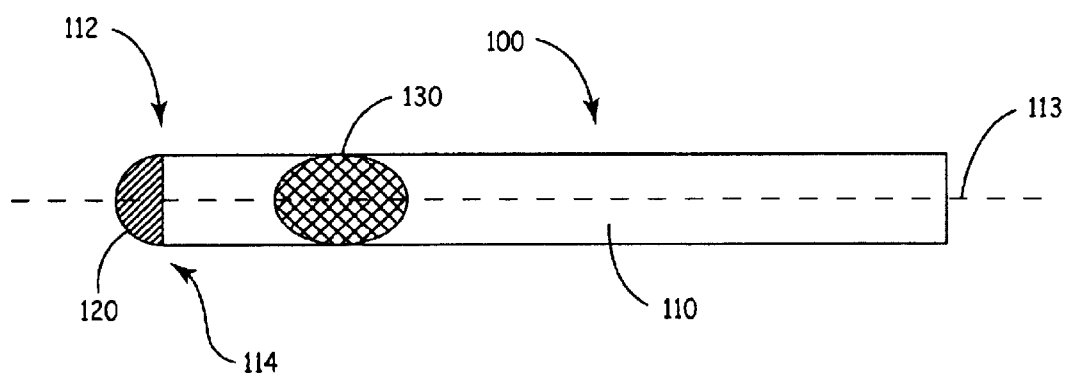
FIG. 2 is a plan view of an illustrative acoustic ablation catheter including an ablation electrode and a detection sensor according to another embodiment of the present invention.

FIG. 2 is a plan view of an illustrative acoustic ablation catheter 100 according to one embodiment of the present invention.

As illustrated, acoustic ablation catheter 100 includes a catheter body 110 extending along axis 113 when in at least a non-flexed state and having a distal end 112. The acoustic ablation catheter 100 also includes an ablation electrode 120 extending from the distal end 112 of catheter body 110 at a tip 114, and a detection sensor 130 proximate the distal end 112 of the catheter body 110. The catheter body 110 may be constructed of any suitable material known in the art for catheter bodies, e.g., plastic, silicon, Although depicted as embedded within the catheter body 110, the ablation electrode 120 may also be fixed on a surface of the catheter body 110.

The ablation electrode 120 is in communication with an ablation energy generator (e.g., ablation energy generator 12 of FIG. 1) through any suitable wire and/or cable known in the art that is contained within the catheter body 110. During ablation, the ablation electrode 120 is operable to direct electromagnetic energy to tissue by contacting the ablation electrode 120 with the tissue to be ablated.

Although depicted as being at the tip 114 of the catheter body 110, the location of the ablation electrode 120 may be at other locations on the catheter, e.g., switched with detection sensor 130 such that the detection sensor 130 is located at the tip 114 and the ablation electrode 120 is located proximate the distal end 112.

As indicated above, proximate the ablation electrode 120 and the distal end 112 of catheter body 110 is the detection sensor 130. The detection sensor 130 may be any suitable detection sensor known in the art for detecting various physiological and/or non-physiological parameters. Preferably, the detection sensor 130 is an acoustic sensing element operable to sense acoustical energy and/or ablation temperature as is further described herein. For detecting acoustical energy, the detection sensor 130 may include a microphone such as a capacitor-type microphone, a piezoelectric transducer element, a piezoelectric microphone, an ultrasound transducer, etc.

The use of a microphone for cardiac therapy is known in the art. For example, U.S. Pat. No. 4,763,646 to Lekholm entitled "Heart Pacemaker," issued Aug. 16, 1988, discloses the use of an intracardiac microphone for cardiac pacing control. Such a microphone as described therein may also be used according to the present invention.

Preferably, the detection sensor is a contact microphone. For example, contact microphones are widely used in music, e.g., a piezoelectric film glued to an acoustic guitar body. Contact microphones are also known in the art for use in gnathosonometry, where a microphone has direct contact with a patient's teeth for recording the sounds produced by the patient while chewing.

In order to detect temperature, the detection sensor 130 may be a thermocouple, a piezoelectric transducer element, a piezoelectric film, such as Kynar piezoelectric film, which can provide sound and temperature information, PDF material, etc. Although depicted as embedded within the catheter body 110, the detection sensor 130 may also be fixed on a surface of the catheter body 110.

Figure 3:
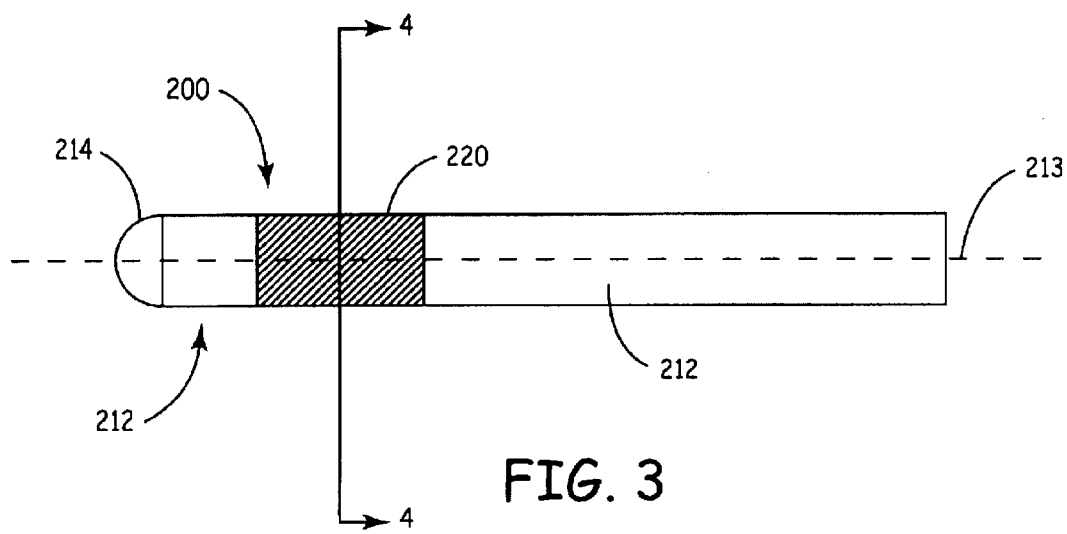
FIG. 3 is a plan view of an illustrative acoustic ablation catheter including an ablation ring electrode according to one embodiment of the present invention.

FIG. 3 illustrates another exemplary embodiment of an acoustic ablation catheter 200 of the present invention. The acoustic ablation catheter 200 includes a catheter body 212 extending along axis 213 at least when in a non-flexed state and includes a distal end 212 terminating in a contoured tip 214. The catheter 200 further includes an ablation electrode 220 (e.g., a ring electrode) proximate the distal end 212 of the catheter body 212, and a detection sensor (not shown in FIG. 3 but included in embodiments of FIGS. 4 and 5). The metal or conductive ring electrode is connected by a wire (not shown) to the ablation generator. When the ablation energy is applied, the ablation electrode 220 may provide an axially symmetric electric field for tissue ablation.

The acoustic ablation catheter 200 is similar to the acoustic ablation catheter 100 illustrated in FIG. 2. Among the differences between the two embodiments is that ablation catheter 200 includes the detection sensor within the ablation ring electrode 220, i.e., inside the catheter body 212 as further illustrated in FIGS. 4 and 5. In contrast to catheter 200, catheter 100 is configured such that the detection sensor 130 is mounted with respect to the exterior of the catheter body 110 as shown in FIG. 2. Further, sound attenuation caused by vibrations traveling through ablation electrode 220 to the detection sensor may be reduced by separating the ablation electrode from the detection sensor as illustrated in FIG. 2.

Figure 4:
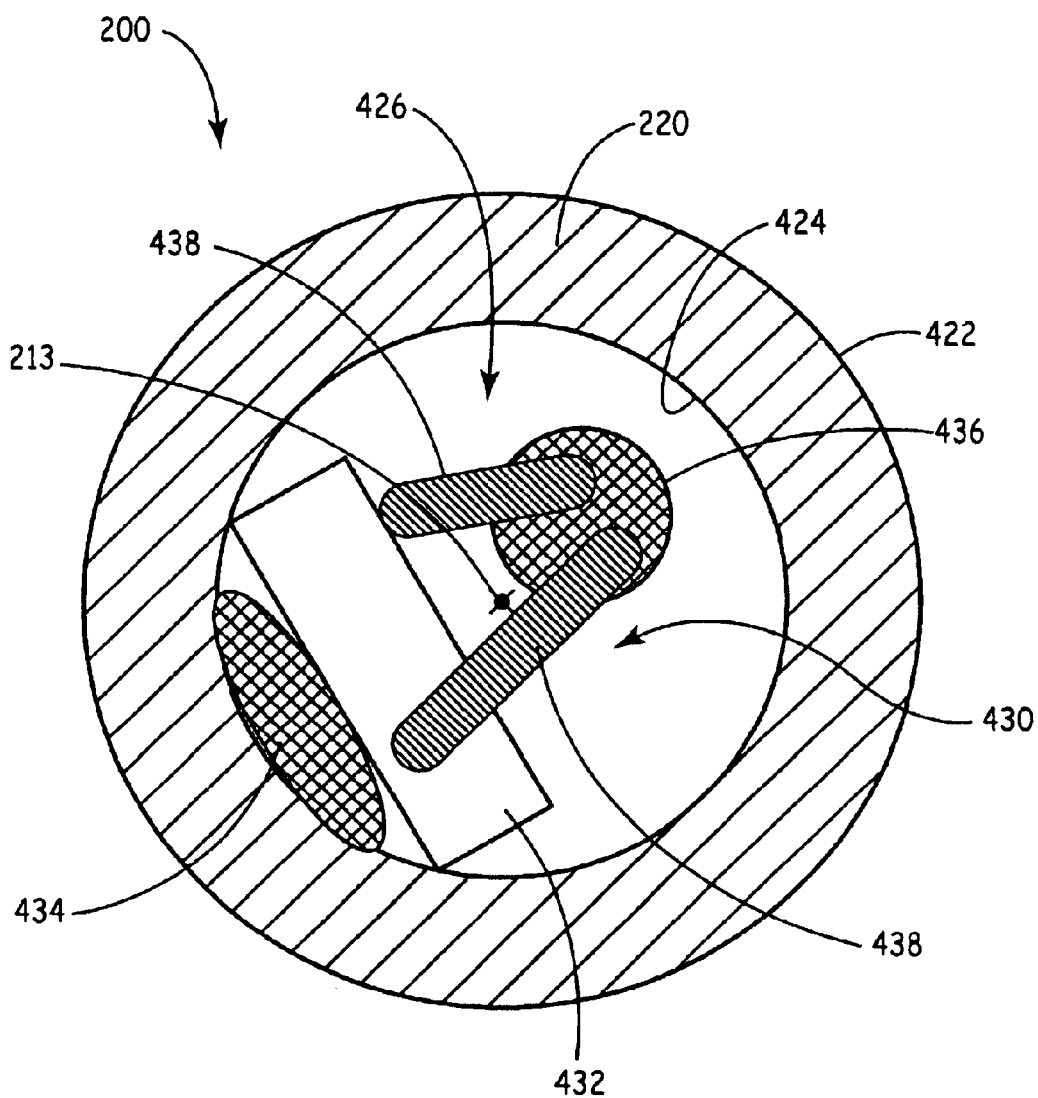
FIG. 4 is a cross-section view of one embodiment of the acoustic ablation catheter of FIG. 3 taken along line 4—4.
Figure 5:
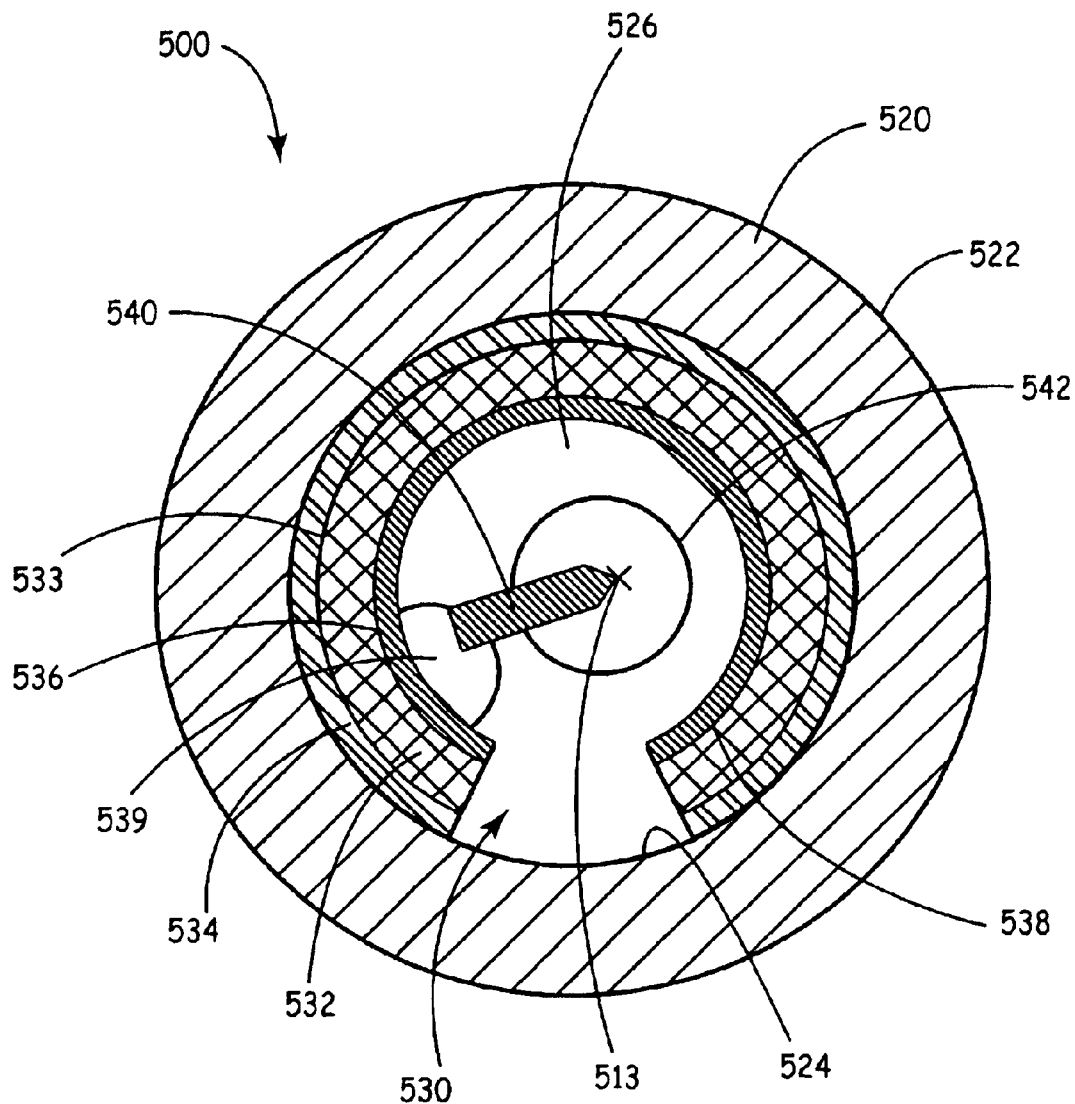
FIG. 5 is a cross-section view of another embodiment of the acoustic ablation catheter of FIG. 3 taken along line 4—4 including an acoustic device proximate an inner volume of the ablation ring electrode.

FIGS. 4–5 illustrate two alternative embodiments of the acoustic ablation catheter 200 in accordance with the present invention. Both are different alternative cross-sections taken along the same line 4—4 of FIG. 3.

As illustrated in FIG. 4, acoustic ablation catheter 200 includes ablation ring electrode 220. The ring electrode 220 includes an outer surface 422 at a radial distance from the axis 213 and an inner surface 424 at a radial distance from the axis 213 that is less than the outer surface 422. The inner surface 424 defines a volume 426 extending along axis 213 within the ablation electrode 220 and catheter body 212.

Located in volume 426 of ablation electrode 220 is detection device 430, which includes a microphone 432 (e.g., a piezoelectric transducer). The microphone 432 may be any suitable microphone known in the art as mentioned above, but is preferably a contact microphone, more preferably a film that can be used to sense sound and temperature. The microphone 432 is acoustically coupled to the inner surface 424 of the ablation electrode 220 by acoustic coupling material 434. Suitable acoustic coupling materials include, but are not limited to, conductive glue, non-conductive glue such as epoxy, etc. In other words, acoustic coupling material 434 may include any suitable material capable of transferring vibrations from the inner surface 424 of the ablation electrode 220 to the microphone 432.

The microphone 432 is in communication with controller circuitry (e.g., of the ablation system 10 of FIG. 1) through wires 438 of cable 436. The cable 436 extends through the body 212 of the catheter 200 with, for example, cable (not shown) for delivering power to the ablation electrode 220.

In operation, for example, acoustical energy may be transmitted to contact microphone 432 by acoustical waves vibrating the ablation electrode 220. The ablation electrode 220 then transmits the vibrations to the contact microphone 432 via acoustic coupling material 434. The microphone 432 is operable to then detect the vibrations and transduce the same for providing a signal representative of the acoustic waves. The signal is transmitted through wires 438 of cable 436 to the controller circuitry for sound analysis as is further described herein. External electronics may be used to amplify the signal received from the microphone 432 (e.g., the piezoelectric film transducer).

Further, acoustic device 430 may also be operable to detect a temperature in the region being ablated. For example, a piezoelectric film may indicate temperature fluctuations by changes in impedance of the film. These changes in impedance may be indicated by an electric signal produced by the piezoelectric film. Further, temperature fluctuations may also be detected by changes in a dielectric constant of the piezoelectric film. Another parameter of piezoelectric film that may be used to detect temperature is the measurement of the dielectric loss tangent. Pyroelectric sensitivity of piezoelectric film is well known in the art, and the material has been used for a variety of commercial applications, including passive infrared imaging arrays and fingerprint sensors. A transducer signal produced by the piezoelectric film may, therefore, be representative of both sensed acoustical energy and sensed temperature.

In the alternate cross-section embodiment of the acoustic ablation catheter of FIG. 3 as illustrated in FIG. 5, the alternate catheter 500 includes (like catheter 200 of FIG. 4) an ablation ring electrode 520. Ablation ring electrode 520 includes an outer radial surface 522 and an inner radial surface 524 along axis 513. The inner surface 524 defines an inner volume 526 extending along the axis 513. The ablation electrode 520 may be made of any suitable materials known in the art for ablation electrodes as described herein.

Located within the inner volume 526 is acoustic sensing device 530. Acoustic sensing device 530 includes a piezoelectric film 532. The piezoelectric film 532 includes a first radial surface 533 and an opposing second radial surface 536. The piezoelectric film 532 is acoustically coupled via the first radial surface 533 to the inner surface 524 of ablation electrode 520 using a conductive adhesive layer 534. The piezolelectric film 532 may be manufactured of any suitable material, including, but not limited to, Kynar, manufactured by Measurement Specialties, Inc. of Fairfield N.J. The conductive adhesive layer 534 may be any suitable conductive adhesive known in the art for transmitting vibrations or acoustic waves and/or electrical current, e.g., conductive glue such as silver filled or gold filled two-component epoxy-based glue.

The second radial surface 536 of piezoelectric film 532 is electrically coupled to a radial metal electrode 538 extending along axis 513, which may include any suitable material. The electrode 538 in turn is electrically coupled to wire 540 of cable 542 using a conductive adhesive 539, which may be manufactured using similar materials to those of other conductive adhesives as described herein. In other words, radial surfaces 533 and 524 may be metallized layers that may function as electrodes of the piezoelectric material 532.

In operation, acoustical waves of sound and the vibrations produced in the vicinity of the ablation electrode 520 are transmitted to the microphone or piezoelectric film 532 through the metal electrode 520 structure. In other words, the ablation electrode 520 vibrates from the acoustic waves in the vicinity thereof. The vibrations of ablation electrode 520 are transmitted through conductive adhesive layer 534 to the piezoelectric film 532. The piezoelectric film 532 transduces or converts the vibrations into a signal representative of the acoustic waves that vibrated the ablation electrode 520. The signal is then provided from the piezoelectric film 532 to the electrode 538 and then to wire 540 of cable 542 and a wire connected to the ablation electrode 520 provides the signal to external circuitry (e.g., amplification circuitry of the controller circuitry 10).

Any acoustic ablation catheters and systems described herein or otherwise known may be configured with a microphone as described herein. Further, any of such ablation catheters may be used with various advantageous methods of acoustically monitored ablation in accordance with the present invention as described herein.

Figure 6:
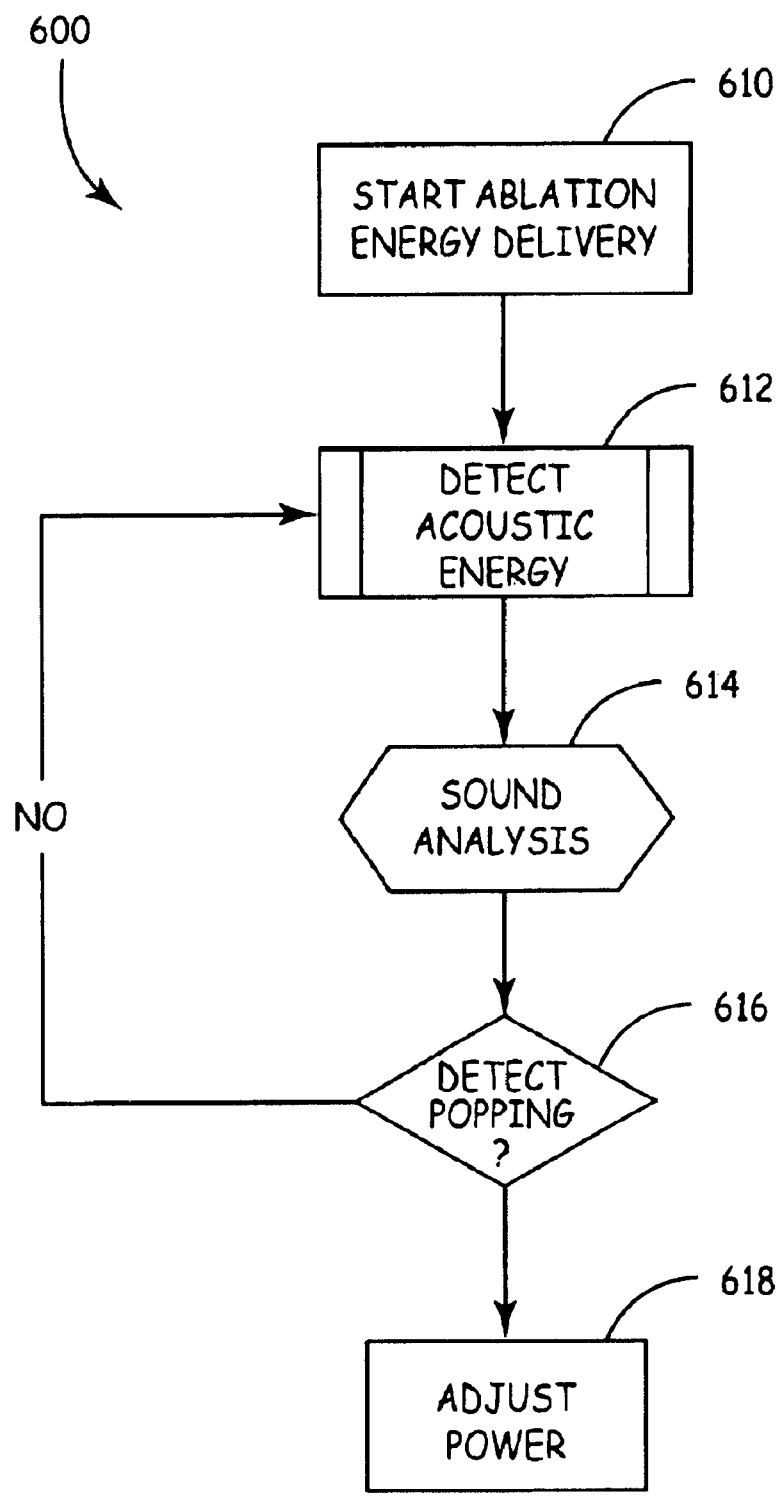
FIG. 6 is a flow diagram illustrating an acoustically monitored ablation method according to one embodiment of the present invention.

FIG. 6 is a flow diagram illustrating an acoustically monitored ablation method 600 according to one exemplary embodiment of the present invention. At 610, ablation energy is delivered to the tissue to be ablated using an acoustic ablation catheter (e.g., acoustic ablation catheter 200 in FIG. 3). In general, an ablation energy generator (e.g., ablation energy generator 12 of FIG. 1) generates electromagnetic energy and directs the energy to the acoustic ablation catheter where it is directed to the tissue by an ablation electrode (e.g., ablation electrode 220).

At 612, acoustical energy is detected using, for example, the detection sensors as described above (e.g., the piezoelectric transducer films 432, 532). A transducer signal is provided for analysis that is representative of the detected acoustical energy. For example, the signal may be amplified and sent for analysis by a programmed processor based controller circuitry.

The transducer signal representative of any sound at the ablation site is analyzed at 614. As described above, directing too much ablation energy to the tissue may cause cells within the tissue to explode. When the cells undesirably explode, the bursting generally produces a popping sound. The popping sound is usually of such intensity that it can be heard even outside of a patient's body.

The sound analysis performed at 614 using methods described in greater detail below determines whether the monitored acoustical energy includes any popping sounds. If popping sounds are detected at 616, the energy being directed to the tissue is reduced and/or even shut off or terminated to prevent undesirable craters from forming. If no popping sounds are detected at 616, the acoustically monitored ablation method 600 returns to detecting acoustical energy at 612.

For example, various methods of sound analysis may be utilized with the ablation methods of the present invention. In general, a transducer signal representative of acoustical energy detected during ablation of tissue may include at least a cardiac generated acoustical energy component representative of cardiac-based sounds (e.g., heart valves closing, blood flow, etc.). By removing this cardiac generated acoustical energy component from the transducer signal, an ablation sound spectrum may be obtained that is representative of sounds caused by the ablation procedure, e.g., cell explosion, the catheter hitting the endocardial wall, etc.

Figure 7:
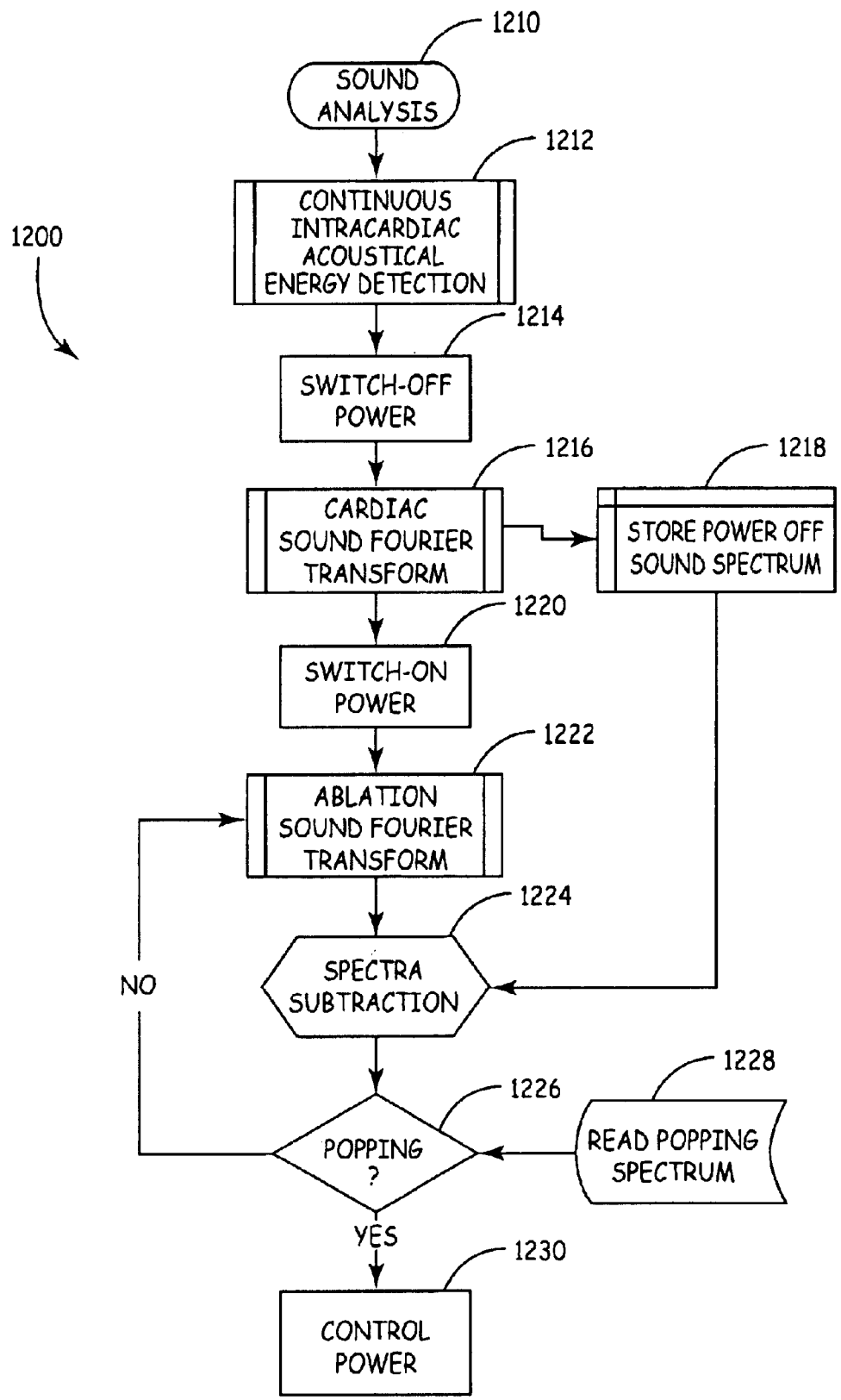
FIG. 7 is a flow diagram illustrating a sound analysis method for use with ablation procedures such as shown in FIG. 6 according to another embodiment of the present invention.

One exemplary sound analysis method 1200 is illustrated in the flow diagram of FIG. 7. The method 1200 may be utilized with any of the acoustically monitored ablation methods described herein and with one of any of the catheters also described herein.

At 1210, sound analysis begins. Acoustical energy (i.e., sound waves) is continuously monitored (although sampling may be used) at 1212 and a transducer signal is provided that is representative of the detected acoustical energy whether or not the ablation power generator (e.g., generator 12) is turned on or off. At 1214, electromagnetic energy (e.g., RF energy) that is directed to tissue to be ablated is shut off or discontinued. The transducer signal representative of acoustical energy that is detected after ablation is discontinued at 1214 is then generally representative of cardiac-based sounds such as intracardiac physiologic sounds (e.g., heart valves closing, blood flow, etc.) and/or sounds produced by the catheter hitting the endocardial wall, sliding against the endocardial wall, etc. This transducer signal is then transformed into a cardiac sound Fourier spectrum using Fourier analysis techniques that are well known in the art at 1216. The cardiac sound Fourier spectrum produced at 1216 may then be stored at 1218 for later use (e.g., in the controller circuitry).

At 1220, the ablation procedure may be resumed by providing electromagnetic energy to the tissue to be ablated. At 1222, a Fourier transform, for example, is performed on the transducer signal representative of acoustic waves that are sensed during the ablation procedure. The resulting ablation sound spectrum is compared with the stored cardiac sound spectrum at 1224 (e.g., the cardiac sound spectrum is subtracted from the ablation sound spectrum). For example, the ablation sound spectrum (if no destruction or popping is occurring) should remain almost the same as the cardiac sound spectrum except for some low-volume additional noise that is produced by tissue modification due to the application of ablation energy to the tissue.

In other words, the ablation sound spectrum is extracted by removing the cardiac sound spectrum. The extracted signal may be transformed for analysis by any suitable mathematical methods such that the transformed signal may be used for comparison, correlation to other signals, or any other analysis technique.

For example, the transducer signal may be due to a low-volume noise spectrum. However, if the subtraction result of the spectra suddenly changes, then the change from the substantially lower volume noise spectrum to a resulting spectrum that is quite different is likely a result of or caused by crater formation and/or popping sounds occurring from explosion of tissue cells.

At 1226, the method 1200 determines whether the resultant spectrum includes popping sounds. A predetermined acoustic profile of a popping sound, i.e., popping spectrum profile, may be stored at 1228 and compared to the resultant spectrum at 1226. Alternatively, a simple threshold spectrum may be used to detect popping sounds.

If popping sounds are detected, then the provision of electromagnetic energy to the tissue being ablated is controlled at 1230, e.g., reduced, terminated, etc. If no popping sounds are detected, then the method 1200 returns to analysis at 1222.

Although Fourier transformation is used in method 1200, other mathematical methods used in signal analysis may be utilized in this method and other methods described herein, such as those used to detect instability of the catheter, e.g., wavelet transformation, autocorrelation, cross-correlation, etc.

Acoustic monitoring of ablation therapy may also be utilized to aid in determining whether an ablation catheter is stable when implanted in, e.g., a heart. For example, if detected acoustical energy is synchronized with a QRS wave of an EGG waveform, e.g., if the detected acoustical energy includes sounds that rhythmically occur after the QRS wave at a given time interval, the sounds may be caused by the catheter striking an inner wall of the heart with each heart contraction. This catheter "floating" is contrasted to when the catheter is in constant contact with the heart wall. An unstable catheter will have a characteristic sound that may be analyzed and some sort of warning device may be activated to indicate to a practitioner that the catheter is floating within the heart.

Figure 8:
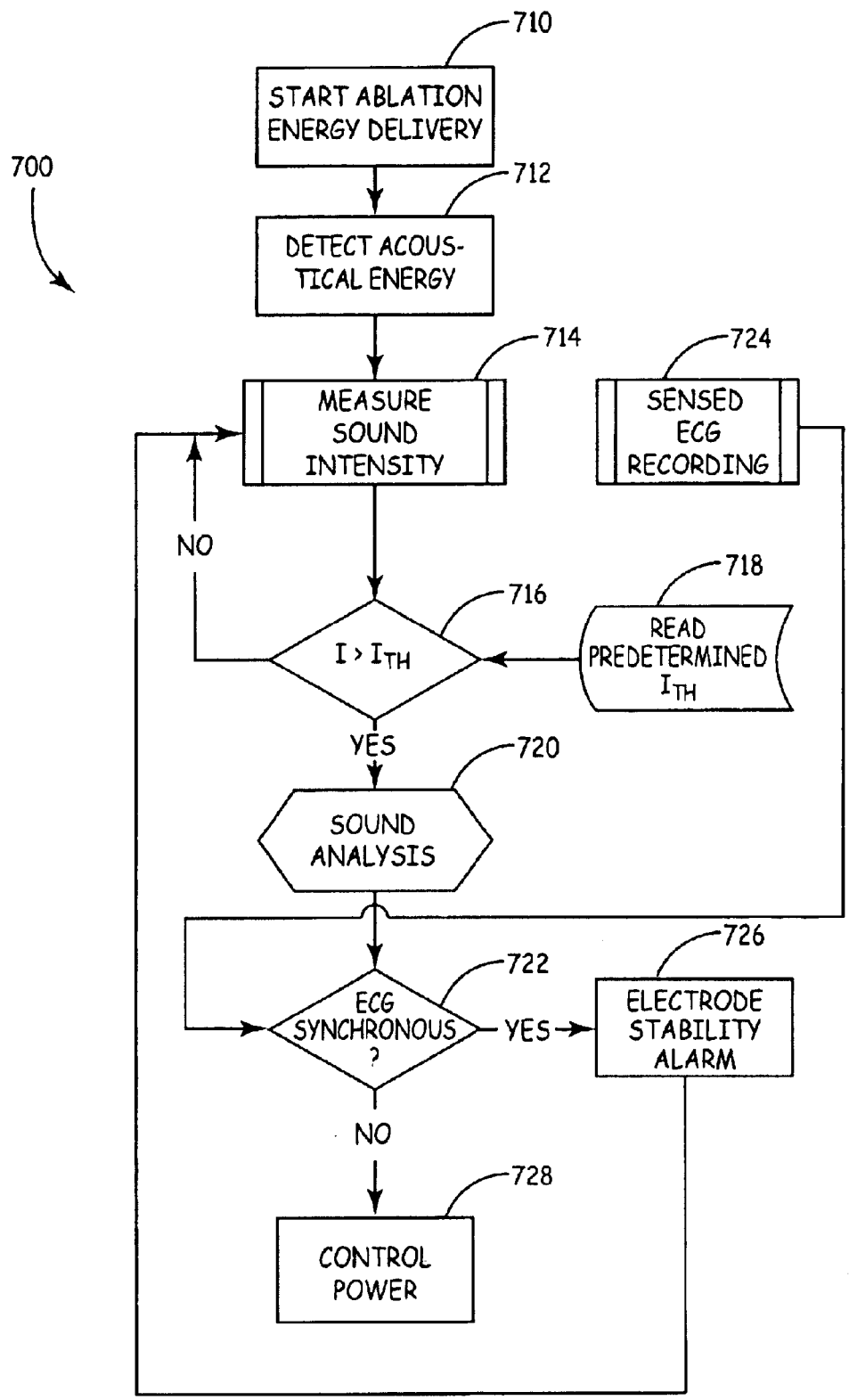
FIG. 8 is a flow diagram illustrating an acoustically monitored ablation method in relation to an ECG waveform according to another embodiment of the present invention.

FIG. 8 is a flow diagram illustrating an acoustically monitored ablation method 700 in relation to a ECG waveform according to one embodiment of the present invention that may be used to determine the stability of an ablation catheter (e.g., acoustic ablation catheters as illustrated above). At 710, electromagnetic energy is delivered to tissue that is to be ablated (e.g., using ablation energy generator 12 and ablation electrode 14 as illustrated in FIG. 1 and described above). At 712, acoustical energy is detected and a transducer signal is provided that is representative of the detected acoustical energy. At 714, sound intensity is measured using the transducer signal and an initial analysis is used to determine whether a sound analysis should be performed, e.g., whether the transducer signal is representative of noise or whether additional acoustical energy that may be representative of further desired information such as catheter stability is present.

For example, in the illustrative embodiment of FIG. 8, the measured sound intensity is compared to a predetermined sound intensity threshold $I_{TH}$ at 716, where $I_{TH}$ may be a programmed predetermined value read from memory (block 718). If the measured sound intensity is less than $I_{TH}$, acoustically monitored ablation method 700 continues with further detection of acoustical energy at 712. If, however, the measured sound intensity is greater than $I_{TH}$, the transducer signal is analyzed at 720 using one or more various methods described in greater detail herein, e.g., using Fourier transformation, wavelet transformation, etc., to remove cardiac sounds such as those caused by valve action.

Further, for example, at 722, the sound sensed by the transducer may be compared to at least a portion of an EGG waveform that is sensed at 724 or otherwise provided. The sound analysis may be performed using numerous signal processing techniques, e.g., spectral analysis, wavelet transform, autocorrelation, etc. If the sound is synchronized with the ECG waveform, then the detected acoustical energy may indicate that the acoustic ablation catheter is floating, i.e., unstable. In the case of instability, the method 700 may trigger an electrode stability alarm at 724 to warn the practitioner of the catheters instability.

If the sound is not synchronized (i.e., asynchronous) with the ECG waveform, then the detected acoustical energy may indicate that ablation may be causing crater formation. Therefore, at 728, the electromagnetic energy being directed to the tissue may be controlled to prevent crater formation, e.g., reduced.

Normally, minor catheter dislocations may cause low-volume sounds that may be tolerated. However, severely unstable catheters that rhythmically lose contact with tissue (e.g., the endocardium) and rhythmically hit the tissue (e.g., endocardial wall) may produce high-volume sounds. If the sounds produced are louder than a certain predetermined value $I_{TH}$, (e.g., block 716) an ablation electrode stability alarm may be triggered (block 726) and the energy provided to the ablation electrode may be controlled (block 728), e.g., reduced or shut off, to prevent thrombus formation around the electrode. If the acoustical energy produced does not repeatedly occur after the cardiac contraction but instead randomly occurs within the cardiac cycle, a sound analysis may then be done in order to determine whether crater formation may be occurring.

Figure 9:
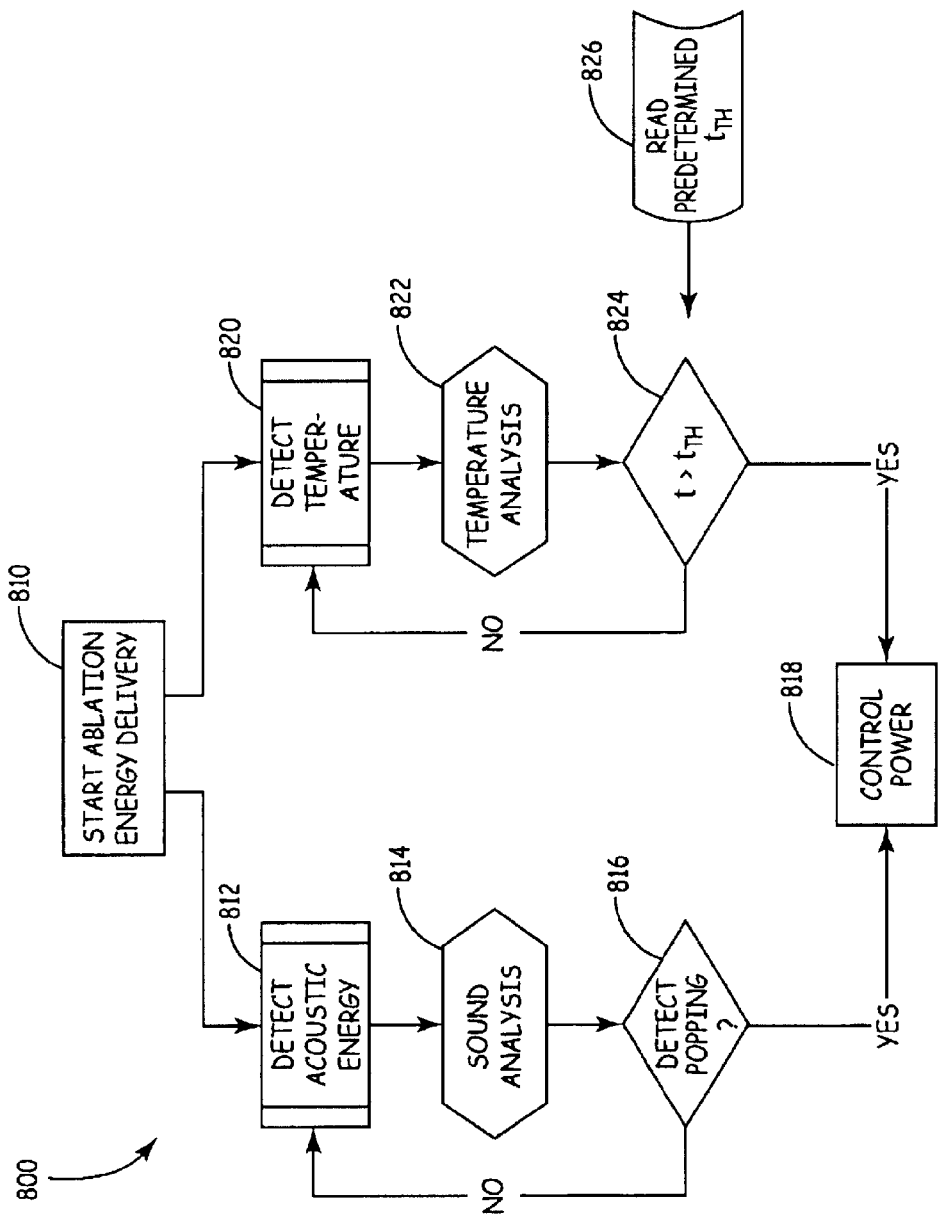
FIG. 9 is a flow diagram illustrating an acoustically monitored ablation method in combination with temperature monitoring and control according to another embodiment of the present invention.

FIG. 9 is a flow diagram illustrating an acoustically monitored ablation method 800 in relation to temperature monitoring and control according to another embodiment of the present invention. As described above, certain types of detection sensors are capable of detecting both acoustical energy and/or temperature and producing a transducer signal representative of the detected acoustical energy and/or the detected temperature. For example, certain piezoelectric microphones may be configured to also detect temperature. Further, temperature is a detection parameter that is well known in the art for controlling ablation of tissue.

The acoustically monitored ablation method 800 includes both acoustical energy detection and ablation temperature detection to aid in preventing crater formation during tissue ablation. At 810, electromagnetic energy is directed to tissue to be ablated. Acoustical energy is detected at 812 and a transducer signal is provided that is representative of the detected acoustical energy. The transducer signal is analyzed at 814, e.g., at least a cardiac generated acoustical energy component is removed therefrom using Fourier transformation, wavelet transformation, etc.

If the analyzed transducer signal includes at least one popping sound as detected at 816, thus probably indicating crater formation, then the electromagnetic radiation being directed to the tissue is controlled at 818, e.g., reduced, such that crater formation ceases. If at least one popping sound is not detected at 816, then method 800 returns to detecting acoustical energy at 812 during the ablation process.

The acoustically monitored ablation method 800 also includes monitoring of ablation temperature to prevent crater formation. At 820, ablation temperature is detected and an ablation temperature signal is provided that is representative of the ablation temperature. At 822, the ablation temperature signal is analyzed using methods known in the art. At 824, the method 800 determines whether the ablation temperature is greater than a predetermined temperature threshold $t_{th}$ that is stored at 826. If yes, then at 818 the electromagnetic energy directed to the tissue is controlled, e.g., reduced, to prevent the occurrence of crater formation. If the ablation temperature is less than $t_{th}$, the method 800 returns to detection of ablation temperature 820.

The detection of both acoustical energy and ablation temperature illustrated in method 800 and control of the ablation energy may occur in sequential order. Preferably, the method 800 detects and controls power output of the ablation electrode using both detected acoustical energy and temperature simultaneously. In other words, the signals may be used separately or in combination to control the ablation process. For example, in addition to those already described herein, the sensing of one parameter, e.g., temperature, may be used to set a more stringent threshold level or levels when analyzing another parameter, e.g., sound. Further, such parameters measured may be correlated with one another such that if events are occurring simultaneously, e.g., an increase in sound level and an increase in temperature, even though not necessarily indicative of an event occurring, may be used to at least sensitize the system and even detect events occurring or about to occur, e.g., popping.

As already described herein, the present invention may utilize acoustical energy to determine both catheter stability and/or crater formation by, for example, comparing acoustical energy to electrocardiograms. Another parameter that may be utilized for determining stability and/or crater formation with the methods and systems already describe is that of mechanical energy or physical motion of the heart produced during atrial and/or ventricular contraction, such as described with reference to FIGS. 10 and 11.

Figure 10:
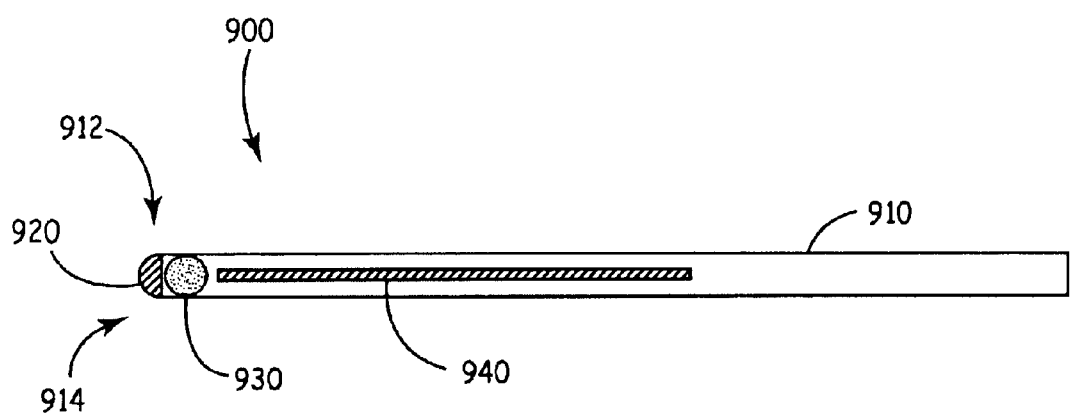
FIG. 10 is a plan view of an illustrative acoustic ablation catheter having a tensiometric element according to another embodiment of the present invention.

FIG. 10 is a plan view of an acoustic ablation catheter 900 having a tensiometric element 940 according to the present invention that may be used to monitor mechanical energy, e.g., movement of the heart during ablation of tissue.

The acoustic ablation catheter includes a catheter body 910, an ablation electrode 920 proximate a tip 914 at the distal end 912 of the catheter body 910, and a detection sensor 930 proximate the distal end 912 of the catheter body 910.

The tensiometric element 940 is preferably mounted within the catheter body 910. For example, such a tensiometric element is described in U.S. Pat. No. 5,261,418 to Ferek-Petric entitled "Cardiac Lead with Tensiometric Element for Providing Signals Corresponding to Heart Contractions," issued Nov. 16, 1993. A cardiac contraction causes the bending of the catheter body 910 and thus the tensiometric element 940. A magnitude of the deflection of catheter body 910 and thus the tensiometric element 940 depends on the radial stiffness of the catheter body 910 and on the force of the heart muscle contraction. The magnitude of deflection also depends on the initial bending forces caused by the implantation position of the catheter 700. A signal representative of the deflection of the tensiometric element 940 is provided.

For example, most implanted catheters have a region of their catheter bodies that are the most exposed to the bending caused by cardiac contractions. This bending section is visible during X-ray diascopy of catheters as is known in the art. In different catheter positions, the magnitude of the bending deflection is different. As disclosed in U.S. Pat. No. 5,261,418 to Ferek-Petric entitled "Cardiac Lead with Tensiometric Element for Providing Signals Corresponding to Heart Contractions," issued Nov. 16, 1993, the tensiometric element 940 may be produced either as a strip or tube that may be manufactured of piezoelectric material or other variable resistance material. A catheter implanted in, for example, a ventricle, will yield a tensiometric signal that is representative of the ventricular contraction, while a catheter implanted in an atrium will yield a tensiometric signal representative of the atrial contraction.

Figure 11:
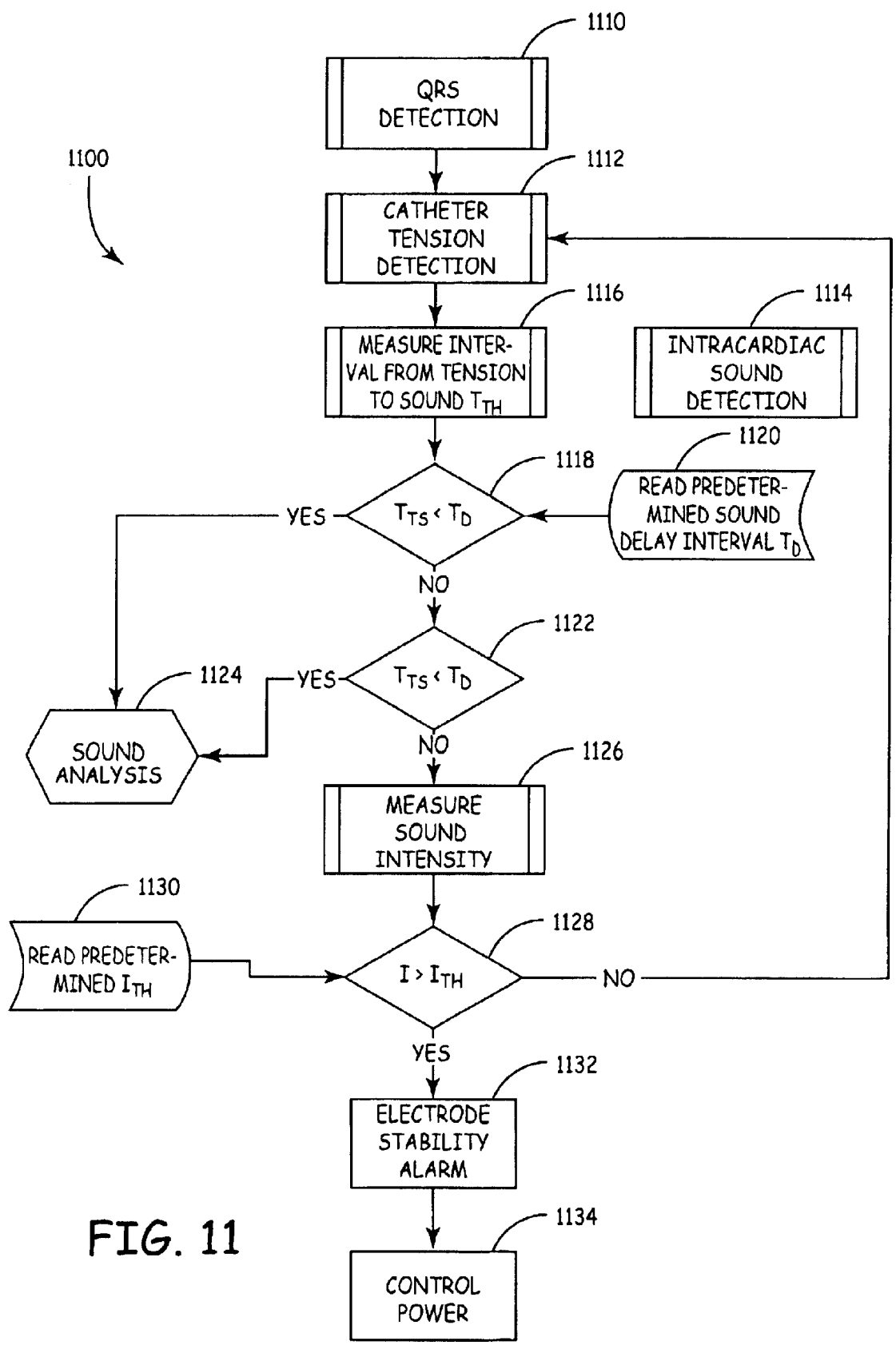
FIG. 11 is a flow diagram illustrating an acoustically monitored ablation method in relation to a tensiometric signal according to another embodiment of the present invention.

FIG. 11 is a flow diagram illustrating an acoustically monitored ablation method in relation to a tensiometric signal according to the present invention. During ablation, an ECG waveform is continuously monitored whereby a QRS wave is detected (block 1110) to yield a reference time. There is a fixed time interval after the QRS wave representative of depolarization of the heart when cardiac contractions occur. The cardiac contraction causes the tensiometric element to be bent. At 1112, this bending results in a tensiometric signal that is representative of the cardiac contraction.

At 1114, acoustical energy is detected and a transducer signal representative of the detected acoustical energy is provided using methods known in the art and described herein. At 1116, a time interval $T_{TS}$ is determined from each detected contraction as represented within the tensiometric signal to each sound event as represented within the transducer signal. If $T_{TS}$ is greater than a predetermined sound delay interval $T_D$ (which is read at 1120), then the method proceeds to sound analysis at 1124 using methods as described herein. Further, if $T_{TS}$ is less than $T_D$, sound analysis at 1124 also occurs. For example, sound analysis as described in reference to FIG. 7 may be performed.

In either case, that $T_{TS}$ is not equal to $T_D$ (within a certain deviation) indicates that the detected acoustical energy is not related to cardiac function, e.g., various heart valves opening and closing, etc. Therefore, the detected acoustical energy represents acoustical energy that may be caused by crater formation due to ablation. In this case, sound analysis at 1124 is used to determine if the detected acoustical energy is representative of the characteristic popping sounds using methods as described herein.

If $T_{TS}$ is equal to $T_D$ (within a certain deviation), then the detected acoustical energy is synchronized with the QRS wave of the ECG waveform. Therefore, the acoustical energy is caused by catheter movement and, most likely, not crater formation.

In other words, during the ablation procedure, an ECG waveform may be continuously monitored whereby a QRS wave is detected to yield a reference time. There may be a fixed time interval after the QRS wave to the depolarization of the heart when a cardiac contraction occurs. The transducer signal from the ablation catheter may also be continuously monitored. Whenever the sequence "cardiac contraction-intracardiac sound" is detected, the interval between the two events may be measured (designated $T_{TS}$). If the transducer signal is synchronized with the QRS wave of the ECG waveform, i.e., the transducer signal always occurs after a certain amount of time delay $T_D$, the sound may be caused by the catheter moving with the cardiac contraction.

Normally, minor catheter dislocations that cause low-volume sound synchronized with heart contractions is tolerable. However, a severely unstable catheter that rhythmically loses contact with the endocardium and rhythmically hits the endocardial wall yields high volume sounds.

As such, at 1126, sound intensity is measured using the transducer signal and, e.g., controller circuitry 10 of FIG. 1. The measured sound intensity is compared to a predetermined sound intensity threshold $I_{TH}$ at 1128, where $I_{TH}$, for example, is read from memory at 1130. If the measured sound intensity is less than $I_{TH}$, then acoustically monitored ablation method 1100 returns to QRS detection at 1112. If, however, the measured sound intensity is greater than $I_{TH}$, the method 1100 triggers an electrode stability alarm at 1132 to indicate to the practitioner that the acoustic ablation catheter is unstable, e.g., a floating catheter. Because of the instability of the acoustic ablation catheter, the electromagnetic energy being directed to the cardiac tissue is controlled at 1134, e.g., reduced and/or shut off to prevent thrombus formation around the electrode.

The complete disclosure of the patents, patent documents, and publications cited in the Background, Detailed Description of Embodiments, and elsewhere herein are incorporated by reference in their entirety as if each were individually incorporated.

The preceding specific embodiments are illustrative of the practice of the invention. It is to be understood, therefore, that other expedients known to those skilled in the art or disclosed herein may be employed without departing from the invention or the scope of the appended claims. For example, the present invention is not limited to internal detection sensors but may be used with detection sensors that are external to the patient. Further, one or more of the ablation methods and/or apparatus may be used in conjunction with one or more other methods and/or apparatus. The present invention is also not limited to implantable ablation catheters per se, but may find further application as other medical devices used for ablation.

What is claimed is:

1. A method for use in ablating tissue, comprising:
    providing a catheter comprising an ablation electrode;
    ablating tissue using the ablation electrode, wherein the ablation electrode directs electromagnetic energy to the tissue;
    detecting at least acoustical energy resulting from the ablation of tissue; and
    comparing the detected acoustical energy to at least a portion of an ECG waveform to determine stability of the catheter.

2. The method of claim 1, wherein comparing the detected acoustical energy to the at least a portion of an ECG waveform comprises:
    detecting acoustical energy over a threshold; and
    determining whether the detected acoustical energy is synchronized with the at least a portion of an ECG waveform.

3. The method of claim 1, wherein the method further comprises controlling the electromagnetic energy directed to the tissue based on the comparison.

4. The method of claim 1, wherein detecting at least acoustical energy further comprises detecting at least acoustical energy resulting from the ablation of tissue using a piezoelectric transducer element.

5. The method of claim 4, wherein the catheter further comprises a catheter body, and further wherein the piezoelectric transducer element is positioned proximate the ablation electrode of the catheter.

6. The method of claim of claim 1, wherein ablating tissue using the ablation electrode further comprises ablating cardiac tissue using the ablation electrode, wherein the ablation electrode directs electromagnetic energy to the cardiac tissue.

7. The method of claim 4, wherein the method further comprises:
    detecting an ablation temperature using the piezoelectric transducer element; and
    controlling the electromagnetic energy directed to the tissue based on the detected ablation temperature.

8. The method of claim 7, wherein the method further comprises simultaneously controlling the electromagnetic energy directed to the tissue based on the detected acoustical energy and the detected ablation temperature.

9. The method of claim 1, wherein the method further comprises:
    analyzing the detected acoustical energy to detect at least one popping sound; and
    reducing the electromagnetic energy directed to the tissue if at least one popping sound is detected.

10. A method for use in ablating tissue, comprising:
    providing a catheter comprising an ablation electrode;
    ablating tissue using the ablation electrode, wherein the ablation electrode directs electromagnetic energy to the tissue;
    detecting acoustical energy and providing a transducer signal representative of the detected acoustical energy during ablation of tissue;
    removing at least a cardiac generated acoustical energy component from the transducer signal; and
    controlling the electromagnetic energy directed to the tissue based on the transducer signal having the at least a cardiac generated acoustical energy component removed therefrom.

11. The method of claim 10, wherein controlling the electromagnetic energy directed to the tissue based on the transducer signal having the at least a cardiac generated acoustical energy component removed therefrom comprises:
    comparing the transducer signal having the at least a cardiac generated acoustical energy component removed therefrom to a predetermined popping sound spectrum to determine the presence of a popping sound; and
    reducing the electromagnetic energy directed to the tissue if at least one popping sound is present.

12. The method of claim 10, wherein removing the at least a cardiac generated acoustical energy component from the transducer signal comprises:
    detecting acoustical energy prior to ablating tissue and providing a pre-ablation transducer signal representative of at least cardiac generated acoustical energy; and subtracting the pre-ablation acoustic signal from the transducer signal provided during tissue ablation.

13. The method of claim 10, wherein detecting acoustical energy further comprises detecting acoustical energy using a piezoelectric transducer element.

14. The method of claim 10, wherein the catheter comprises a catheter body, wherein the piezoelectric transducer is positioned proximate the ablation electrode of the catheter, and further wherein the method further comprises detecting an ablation temperature using the piezoelectric transducer element.

15. The method of claim 14, wherein detecting the ablation temperature using the piezoelectric transducer element comprises measuring a dielectric constant of the piezoelectric transducer.

16. The method of claim 14, wherein detecting the ablation temperature using the piezoelectric transducer element comprises measuring a dielectric loss tangent of the piezoelectric transducer.

17. The method of claim 10, wherein the method further comprises:
   detecting an ablation temperature proximate the tissue being ablated; and
   controlling the electromagnetic energy directed to the tissue based on the detected ablation temperature.

18. The method of claim 17, wherein the method further comprises simultaneously controlling the electromagnetic energy directed to the tissue based on the detected acoustical energy and the detected ablation temperature.

19. A method for use in ablating cardiac tissue, comprising:
   providing a catheter comprising an ablation electrode and a piezoelectric transducer element operable for use in detecting acoustical energy;
   ablating tissue using the ablation electrode, wherein the ablation electrode directs electromagnetic energy to the tissue;
   detecting acoustical energy using the piezoelectric transducer element for detection of at least one popping sound;
   if at least one popping sound is detected, reducing the electromagnetic energy directed to the tissue.

20. The method of claim 19, wherein detecting acoustical energy comprises:
   detecting acoustical energy during ablation of tissue using the piezoelectric transducer element and providing a transducer signal representative of the detected acoustical energy;
   removing at least a cardiac generated acoustical energy component from the transducer signal;
   comparing the transducer signal having the at least a cardiac generated acoustical energy component removed therefrom to an acoustic profile representative of a popping sound; and
   detecting at least one popping sound if the transducer signal having the at least a cardiac generated acoustical energy component removed therefrom matches the acoustic profile.

21. The method of claim 20, wherein removing the at least a cardiac generated acoustical energy component from the transducer signal comprises:
   detecting acoustical energy prior to ablating tissue representative of at least cardiac generated acoustical energy and providing a pre-ablation transducer signal representative of the at least cardiac generated acoustical energy; and
   subtracting the pre-ablation transducer signal from the transducer signal detected during ablation of tissue.

22. The method of claim 19, wherein the method further comprises detecting an ablation temperature proximate the tissue being ablated using the piezoelectric transducer element.

23. The method of claim 22, wherein the method further comprises reducing the electromagnetic energy directed to the tissue based on the ablation temperature.

24. A method for use in ablating tissue, comprising;
   providing a catheter comprising an ablation electrode and a piezoelectric transducer element;
   ablating cardiac tissue using the ablation electrode, wherein the ablation electrode directs electromagnetic energy to the cardiac tissue;
   detecting acoustical energy during ablation of cardiac tissue using the piezoelectric transducer element and providing a transducer signal representative thereof, wherein the transducer signal is further representative of an ablation temperature proximate tissue being ablated; and
   controlling the electromagnetic energy directed to the tissue based on the transducer signal.

25. The method of claim 24, wherein detecting acoustical energy further comprises simultaneously detecting acoustical energy and temperature using the piezoelectric transducer element.

26. The method of claim 24, wherein detecting acoustical energy using the piezoelectric transducer element further comprises:
   removing at least a cardiac generated acoustical energy component from the transducer signal;
   comparing the transducer signal having the at least a cardiac generated acoustical energy component removed therefrom to an acoustic profile representative of a popping sound; and
   detecting at least one popping sound based on the transducer signal having the at least a cardiac generated acoustical energy component removed therefrom.

27. The method of claim 26, wherein removing the at least a cardiac generated acoustical energy component from the transducer signal comprises:
   detecting acoustical energy prior to ablating tissue and providing a pre-ablation transducer signal representative of at least cardiac generated acoustical energy; and
   subtracting the pre-ablation transducer signal from the transducer signal representative of acoustical energy during ablation of tissue.

28. The method of claim 26, wherein controlling the electromagnetic energy directed to the tissue based on the transducer signal further comprises reducing the electromagnetic energy directed to the tissue if at least one popping sound is detected.

29. The method of claim 24, wherein controlling the electromagnetic energy directed to the tissue based on the transducer signal further comprises reducing the electromagnetic energy directed to the tissue based on the ablation temperature.

30. A method for use in ablating tissue, comprising:
   providing a catheter comprising an ablation electrode;
   ablating tissue using the ablation electrode, wherein the ablation electrode directs electromagnetic energy to the tissue;
   detecting acoustical energy and providing a transducer signal representative of the detected acoustical energy;

measuring a sound intensity of the detected acoustical energy;

comparing the measured sound intensity to a sound intensity threshold;

if the measured sound intensity is greater than the sound intensity threshold, then comparing the transducer signal to at least a portion of an ECG waveform; and reducing the electromagnetic energy directed to the tissue if the transducer signal and the at least a portion of an ECG waveform are asynchronous.

31. The method of claim 30, wherein the method further comprises triggering an electrode stability alarm if the transducer signal and the at least a portion of an ECG waveform are synchronous.

32. A method for use in ablating cardiac tissue, comprising:

providing a catheter comprising an ablation electrode and a tensiometric element;

ablating tissue using the ablation electrode, wherein the ablation electrode directs electromagnetic energy to the cardiac tissue;

detecting a plurality of cardiac contractions using the tensiometric element and providing a tensiometric signal representative of the plurality of cardiac contractions;

detecting acoustical energy and providing a transducer signal representative of the detected acoustical energy;

comparing the tensiometric signal to the transducer signal; and controlling the electromagnetic energy directed to the cardiac tissue based on the compared tensiometric signal and transducer signal.

33. The method of claim 32, wherein the detected acoustic energy comprises a plurality of sound events, wherein comparing the tensiometric signal to the transducer signal further comprises measuring a time interval between at least one sound event and at least one cardiac contraction.

34. The method of claim 33, wherein the method further comprises triggering an electrode stability alarm if the time interval is equal to a predetermined threshold delay interval.

35. The method of claim 33, wherein the method further comprises analyzing the transducer signal if the time interval is not equal to a predetermined threshold delay interval.

36. The method of claim 35, wherein analyzing the transducer signal further comprises:

removing at least a cardiac generated acoustical energy component from the transducer signal; and comparing the transducer signal having the at least a cardiac generated acoustical energy component removed therefrom to an acoustic profile representative of a popping sound to detect at least one popping sound.

37. The method of claim 36, wherein removing the at least a cardiac generated acoustical energy component from the transducer signal comprises:

detecting acoustical energy prior to ablating tissue and providing a pre-ablation transducer signal representative of at least cardiac is generated acoustical energy; and subtracting the pre-ablation transducer signal from the transducer signal representative of acoustical energy during ablation of tissue.

38. The method of claim 37, wherein controlling the electromagnetic energy directed to the cardiac tissue further comprises reducing the electromagnetic energy directed to the cardiac tissue if at least one popping sound is detected.

* * * * *

UNITED STATES PATENT AND TRADEMARK OFFICE
CERTIFICATE OF CORRECTION

PATENT NO. : 6,709,432 B2
DATED : March 23, 2004
INVENTOR(S) : Bozidar Ferek-Petric It is certified that error appears in the above-identified patent and that said Letters Patent is hereby corrected as shown below:

Title page,
Item [54], Title, delete "METHODS" and insert -- METHOD --.
Item [75], Inventors, delete "Ferek-Patric" and insert -- Ferek-Petric --.

Column 20,
Line 25, after "cardiac" please delete "is".

Signed and Sealed this

Twenty-first Day of December, 2004

JON W. DUDAS
*Director of the United States Patent and Trademark Office*